United States Patent
Duarte

(10) Patent No.: US 11,596,518 B2
(45) Date of Patent: Mar. 7, 2023

(54) BONE CAGE INCLUDING OFFSET SETS OF PROTRUSIONS WITHIN A BONE INGROWTH CAVITY AND RELATED METHODS

(71) Applicant: Luis E. Duarte, San Angelo, TX (US)

(72) Inventor: Luis E. Duarte, San Angelo, TX (US)

(*) Notice: Subject to any disclaimer, the term of this patent is extended or adjusted under 35 U.S.C. 154(b) by 225 days.

(21) Appl. No.: 17/120,811

(22) Filed: Dec. 14, 2020

(65) Prior Publication Data

US 2021/0093456 A1 Apr. 1, 2021

Related U.S. Application Data

(62) Division of application No. 15/720,126, filed on Sep. 29, 2017, now Pat. No. 10,893,945.

(51) Int. Cl.
| | |
|---|---|
| A61F 2/44 | (2006.01) |
| A61F 2/46 | (2006.01) |
| A61B 17/86 | (2006.01) |
| A61B 17/70 | (2006.01) |
| A61F 2/30 | (2006.01) |

(52) U.S. Cl.
CPC .......... *A61F 2/30771* (2013.01); *A61F 2/447* (2013.01); *A61F 2/4455* (2013.01); *A61F 2/4465* (2013.01); *A61F 2002/30011* (2013.01); *A61F 2002/3093* (2013.01); *A61F 2002/30593* (2013.01); *A61F 2002/30622* (2013.01); *A61F 2002/30754* (2013.01); *A61F 2002/30772* (2013.01); *A61F 2002/30879* (2013.01); *A61F 2002/30881* (2013.01); *A61F 2002/30884* (2013.01); *A61F 2002/30891* (2013.01); *A61F 2002/30892* (2013.01); *A61F 2002/30894* (2013.01); *A61F 2310/00023* (2013.01); *A61F 2310/00161* (2013.01)

(58) Field of Classification Search
None
See application file for complete search history.

(56) References Cited

U.S. PATENT DOCUMENTS

| | | | |
|---|---|---|---|
| 6,090,143 A | 7/2000 | Meriwether et al. | |
| 6,126,689 A | 10/2000 | Brett | |
| 6,159,244 A * | 12/2000 | Suddaby | A61F 2/4611 606/247 |
| 6,206,924 B1 | 3/2001 | Timm | |
| 6,454,806 B1 * | 9/2002 | Cohen | A61F 2/4465 623/17.15 |

(Continued)

FOREIGN PATENT DOCUMENTS

| | | |
|---|---|---|
| WO | 2016029254 | 3/2016 |
| WO | 2017060413 | 4/2017 |

*Primary Examiner* — Ann Schillinger
(74) *Attorney, Agent, or Firm* — Allen, Dyer, Doppelt + Gilchrist, P.A.

(57) ABSTRACT

A bone cage may include first and second spaced apart frames defining a bone ingrowth cavity therebetween, a plurality of first protrusions each having a proximal end coupled to the first frame and a distal end extending into the cavity toward the second frame but not contacting the second frame, and a plurality of second protrusions each having a proximal end coupled to the second frame and a distal end extending into the cavity toward the first frame but not contacting the first frame. Furthermore, the distal ends of the first protrusions may be laterally offset from the distal ends of the second protrusions.

18 Claims, 3 Drawing Sheets

(56) References Cited

U.S. PATENT DOCUMENTS

| | | | | |
|---|---|---|---|---|
| 6,527,803 B1* | 3/2003 | Crozet | A61F 2/442 | |
| | | | 606/31 | |
| 6,770,095 B2* | 8/2004 | Grinberg | A61F 2/4425 | |
| | | | 623/17.14 | |
| 7,303,565 B2* | 12/2007 | Buttermann | A61B 17/1604 | |
| | | | 606/86 R | |
| 7,537,612 B2* | 5/2009 | Kunzler | A61F 2/4425 | |
| | | | 623/17.13 | |
| 7,563,286 B2* | 7/2009 | Gerber | A61F 2/4425 | |
| | | | 623/17.14 | |
| 7,678,148 B2* | 3/2010 | Peterman | A61F 2/4455 | |
| | | | 623/17.11 | |
| 7,682,396 B2* | 3/2010 | Beaurain | A61F 2/4425 | |
| | | | 623/17.14 | |
| 7,824,445 B2* | 11/2010 | Biro | A61F 2/442 | |
| | | | 623/17.15 | |
| 7,988,733 B2 | 8/2011 | Shimp et al. | | |
| 8,123,809 B2* | 2/2012 | Melkent | A61F 2/44 | |
| | | | 623/17.11 | |
| 8,152,852 B2* | 4/2012 | Biyani | A61F 2/44 | |
| | | | 623/17.16 | |
| 9,072,720 B2 | 7/2015 | Voor et al. | | |
| 9,402,733 B1 | 8/2016 | To et al. | | |
| 9,439,948 B2 | 9/2016 | Lin et al. | | |
| 9,456,907 B1* | 10/2016 | Castro | A61F 2/447 | |
| 9,801,733 B2* | 10/2017 | Wolters | A61F 2/447 | |
| 10,426,634 B1* | 10/2019 | Al-Jazaeri | A61F 2/447 | |
| 2004/0039448 A1* | 2/2004 | Pisharodi | A61F 2/4425 | |
| | | | 623/17.15 | |
| 2006/0241762 A1* | 10/2006 | Kraus | A61F 2/44 | |
| | | | 623/17.11 | |
| 2010/0152856 A1* | 6/2010 | Overes | A61B 17/748 | |
| | | | 623/17.16 | |
| 2011/0144764 A1 | 6/2011 | Bagga et al. | | |
| 2011/0196495 A1 | 8/2011 | Hunt | | |
| 2011/0282392 A1 | 11/2011 | Murphy et al. | | |
| 2016/0213483 A1 | 7/2016 | To et al. | | |
| 2016/0302940 A1 | 10/2016 | To et al. | | |
| 2017/0020685 A1 | 1/2017 | Geisler et al. | | |

* cited by examiner

//BONE CAGE INCLUDING OFFSET SETS OF PROTRUSIONS WITHIN A BONE INGROWTH CAVITY AND RELATED METHODS

TECHNICAL FIELD

The present disclosure relates to the field of medical devices, and more particularly to bone cages and related methods.

BACKGROUND

Cages are used in bone fusion procedures to maintain desired spacing between bones. One example cage is a spinal cage, which may be used to maintain the desired foraminal height between adjacent vertebrae. Cages may also be used between other bones in the body as well.

Generally speaking, bone cages are made from a biocompatible material such as metal (e.g., titanium) or carbon fiber. Some cages also have openings or surface features which help promote bone ingrowth from adjacent bones, which thereby holds or fuses the bones with the cage.

One example of a cage for facilitating fusion of bones, such as vertebrae, or fusion of adjacent bone surfaces is set forth in US 2011/0282392 to Murphy. In one form, the cage includes a plurality of spaced apart walls including a biodegradable polymeric material (e.g., polycaprolactone), an osteoconductive mineral coating (e.g., a calcium compound) on at least a portion of the walls, and a bioactive agent (e.g., a bone morphogenetic protein) associated with the polymeric material and/or the coating. The bioactive agent is present in an amount that induces ossification between the bones or adjacent bone surfaces. The cage may also include a fixation plate connected to at least one of the walls.

US 2011/0196495 to Hunt discloses an implant for interfacing with a bone structure having a web structure including a space truss. The space truss includes two or more planar truss units having a plurality of struts joined at nodes, and the web structure is configured to interface with human bone tissue.

Despite the existence of such systems, further advancements in bone cages may be desirable in certain applications.

SUMMARY

A bone cage may include first and second spaced apart frames defining a bone ingrowth cavity therebetween, a plurality of first protrusions each having a proximal end coupled to the first frame and a distal end extending into the cavity toward the second frame but not contacting the second frame, and a plurality of second protrusions each having a proximal end coupled to the second frame and a distal end extending into the cavity toward the first frame but not contacting the first frame. Furthermore, the distal ends of the first protrusions may be laterally offset from the distal ends of the second protrusions.

In accordance with a first example, at least some of the first and second protrusions extend into the cavity at different angles. In another example implementation, at least some of the first and second protrusions may extend into the cavity normal to the first and second frames, respectively. Furthermore, at least some of the distal ends of the first and second protrusions may extend past one another, for example. In other example embodiments, at least some of the first and second protrusions may have different widths and/or different lengths.

The first and second spaced apart frames may be opposing upper and lower frames in one example. In accordance with another example, the first and second spaced apart frames may be opposing side frames. Also by way of example, the first and second frames and the first and second protrusions may comprise at least one of plastic, carbon fiber, and titanium.

A related method is also provided which may include installing a bone cage, such as the one described briefly above, between adjacent bones in a patient (e.g., vertebrae, etc.).

DETAILED DESCRIPTION OF THE EMBODIMENTS

The present description is made with reference to the accompanying drawings, in which exemplary embodiments are shown. However, many different embodiments may be used, and thus the description should not be construed as limited to the particular embodiments set forth herein. Rather, these embodiments are provided so that this disclosure will be thorough and complete. Like numbers refer to like elements throughout, and prime notation and multiple prime notation are used to indicate similar elements in different embodiments.

Figure 1:
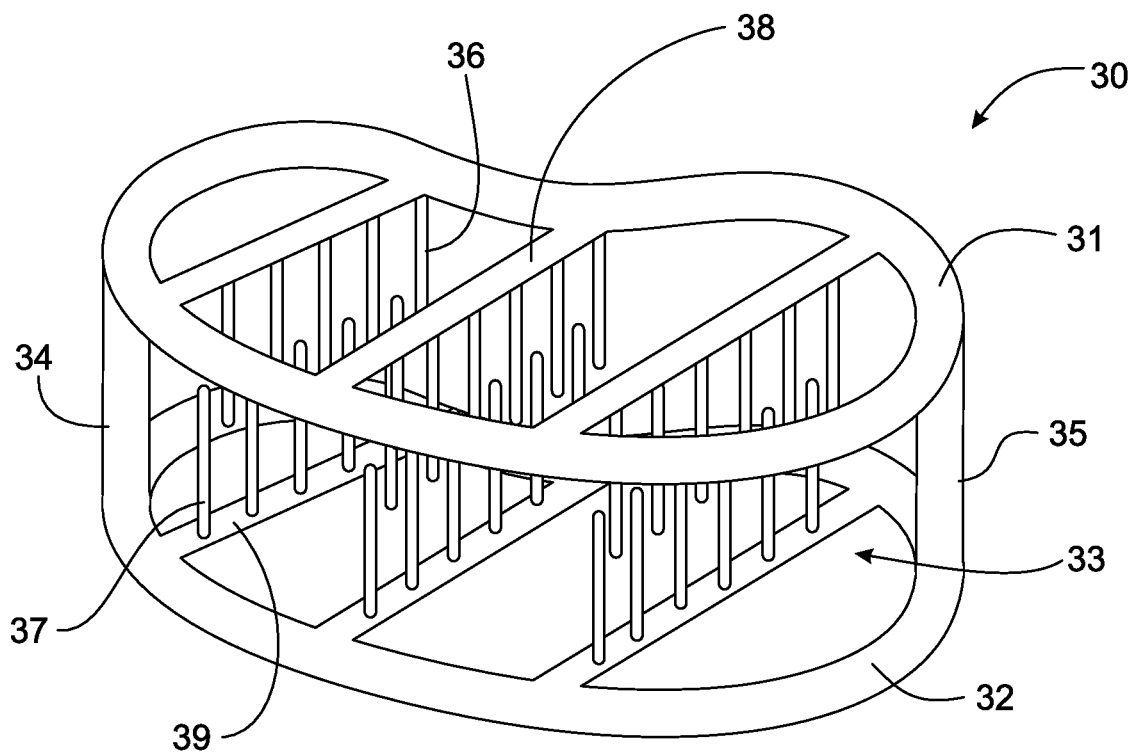
FIG. 1 is a perspective view of a bone cage in accordance with an example embodiment.
Figure 2:
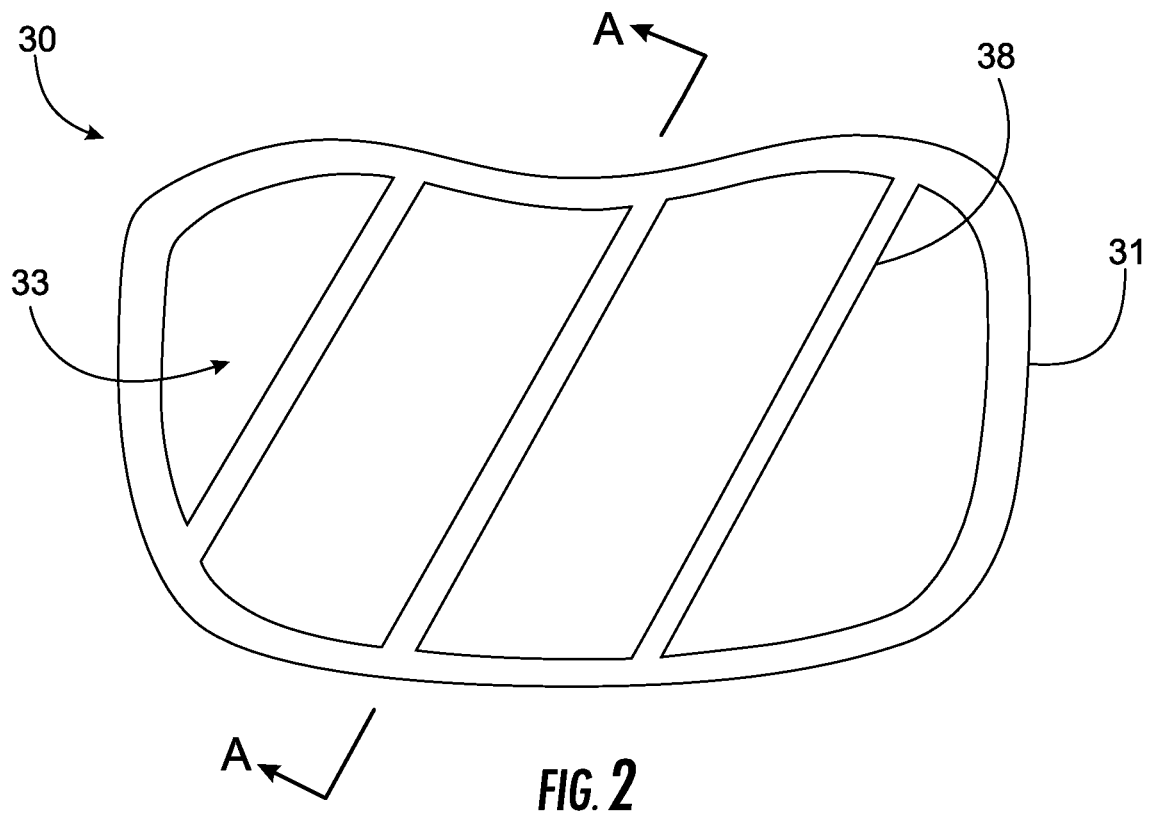
FIG. 2 is a top view of the bone cage of FIG. 1.
Figure 3:
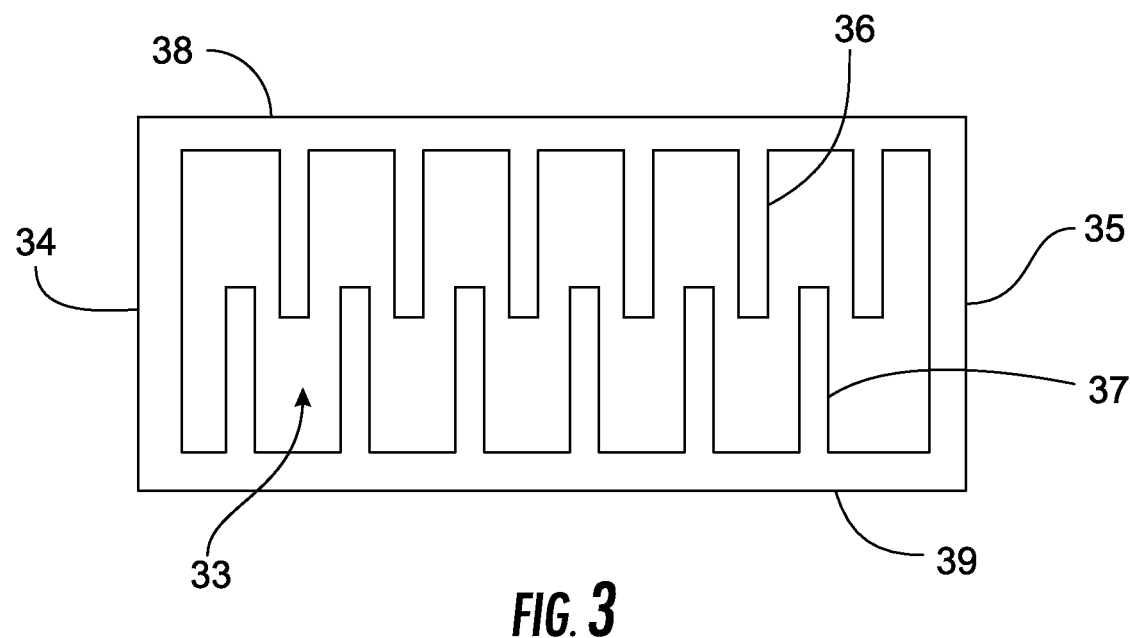
FIG. 3 is a cross-sectional view of the bone cage of FIG. 2 taken along line A-A.

Referring initially to FIGS. 1-3, an interbody fusion or bone cage 30 is first described. The bone cage 30 illustratively includes first and second spaced apart frames 31, 32 defining a bone ingrowth cavity 33 therebetween. In the illustrated example, the first and second spaced apart frames 31, 32 are upper and lower frames, respectively, and the bone cage 30 further illustratively includes side frames 34, 35. The side frames 34, 35 connect the upper and lower frames 31, 32 together at the desired spacing. Here, the upper and lower frames 31, 32 generally have a "kidney bean" shape which is advantageous for spinal applications, but other shapes may be used for different applications if desired.

In the illustrated example, the side frames 34, 35 are on opposite sides or ends of the bone cage 30, but in some embodiments there may be more than two side frames spaced around the periphery of the upper and lower frames 31, 32, if desired. Generally speaking, the side frames 34, 35 (and additional side frames, if used) should be sized and positioned to provide desired support in the vertical direction, yet leave enough room for bone ingrowth.

Furthermore, the bone cage 30 also illustratively includes a plurality of first protrusions 36 each having a proximal end coupled to the first (upper) frame 31 and a distal end extending into the bone ingrowth cavity 33 toward the second frame 32, but not contacting the second frame.

Additionally, the bone cage 30 also illustratively includes a plurality of second protrusions 37 having a proximal end coupled to the second frame 32 and a distal end extending into the bone ingrowth cavity 33 toward the first frame 31, but not contacting the first frame. Furthermore, the distal ends of the first protrusions 36 may be laterally offset from the distal ends of the second protrusions 37, as perhaps best seen in FIG. 3.

Furthermore, in the present example the distal ends of the first and second protrusions 36, 37 extend past one another, though again they do not extend all the way to the opposing frame 39, 38, respectively. In this respect, the first and second protrusions are interdigitated, although they need not be in all embodiments.

In the illustrated example, the first protrusions 36 are carried by struts or beams 38 of the upper frame 31 that extend laterally across the top of the bone ingrowth cavity 33. Moreover, the second protrusions 37 are carried by struts or beams 39 of the lower frame 32 which extend laterally below the bone ingrowth cavity 33. In some embodiments, first and second protrusions 36, 37 may also be carried around portions the periphery of the upper and lower frames 31, 32, if desired.

The bone cage 30 and its various components may be fabricated using bio-compatible materials that are suitable for internal use within a human body (or animal in some veterinary applications). By way of example, the bone cage 30 may be fabricated from one or more of a plastic such as polyether ether ketone (PEEK), carbon fiber, and titanium (e.g., titanium-hydroxyapatite structures), although other suitable materials may be used in different embodiments.

Figure 4:
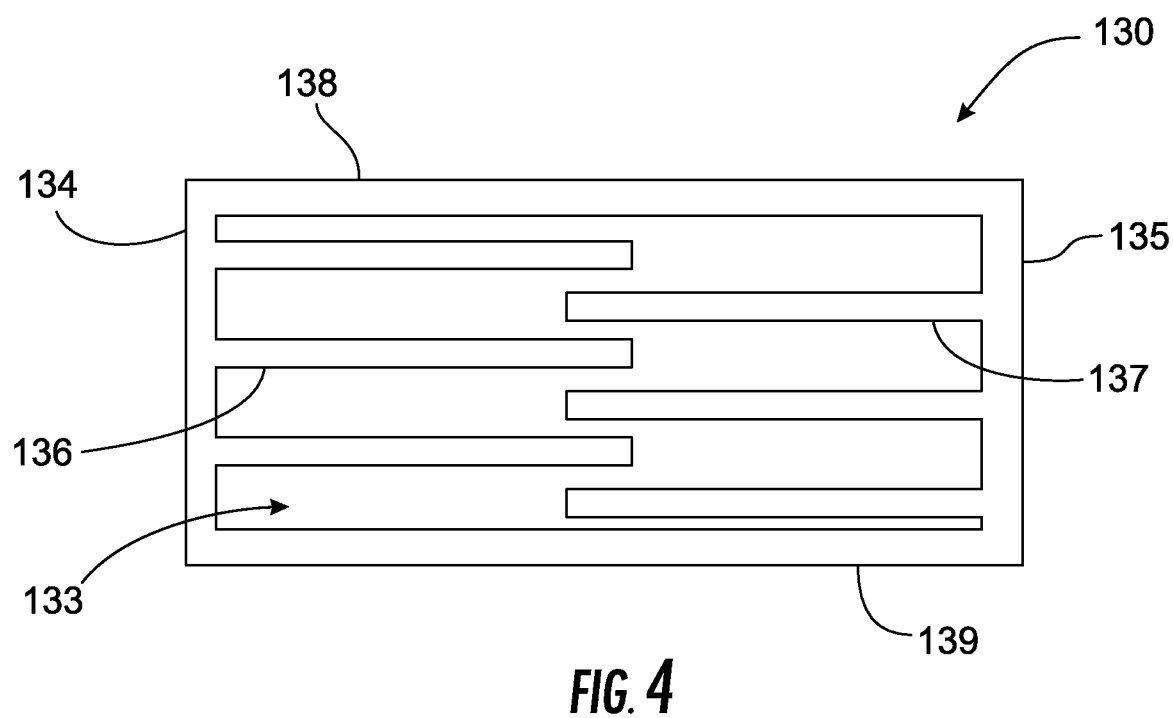
FIG. 4 is a cross-sectional view of another example embodiment of the bone cage of FIG. 2.

Turning now to the embodiment of FIG. 4, in an alternate configuration of the bone cage 130 which includes side frames 134, 135 and upper and lower struts 138, 139 similar to those described above, here the first and second protrusions 136, 137 extend inwardly from the side frames 134, 137, respectively. That is, in this configuration the first and second protrusions 136, 137 extend inwardly from the sides of the bone cage 130 rather from the top and bottom sides, as in FIG. 1. It should be noted that in some embodiments, protrusions may extend from both the upper and lower frames 31, 32 (FIG. 1) as well as the side frames 34, 35 (FIG. 1) or 134, 135 (FIG. 4).

Figure 5:
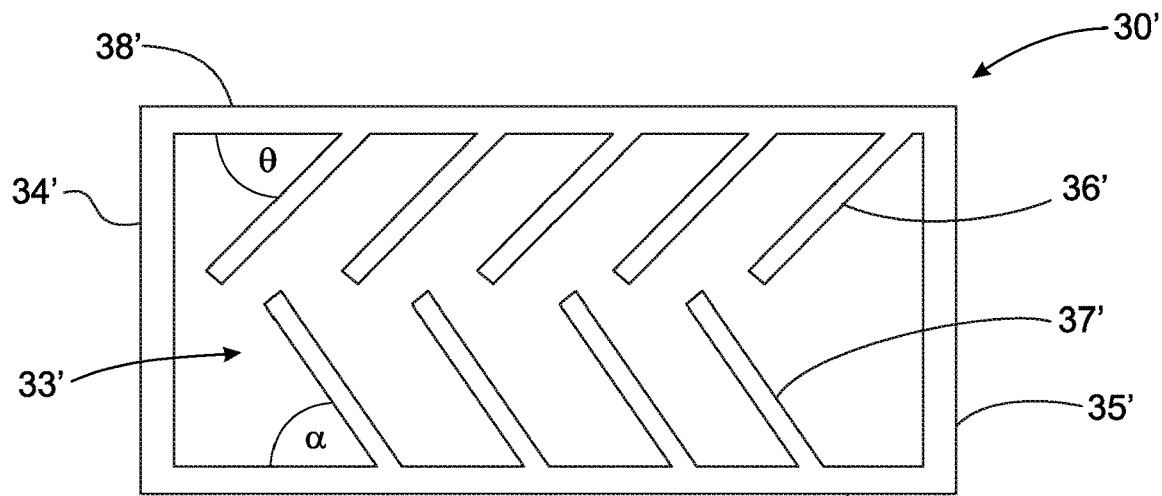
FIG. 5 is a cross-sectional view of still another example embodiment of the bone cage of FIG. 2.

In all of the above-described embodiments, the first and second protrusions 36, 37 and 136, 137 extend into the bone ingrowth cavity normal (i.e., perpendicular) to the upper and lower frames 31, 32 or side frames 34, 35, respectively. However, the protrusions may extend into the bone ingrowth cavity 33 or 133 at different angles in different embodiments, as described now with reference to FIG. 5. More particularly, in the illustrated embodiment of the bone cage 30', the first protrusions 36' extend into the bone ingrowth cavity 33' at an angle θ (which is 45° in the illustrated example), and the second protrusions 37' extend into the bone ingrowth cavity at an angle α different than the angle θ (α is 55° in the illustrated example). However, in different embodiments, different angles may be used.

Figure 6:
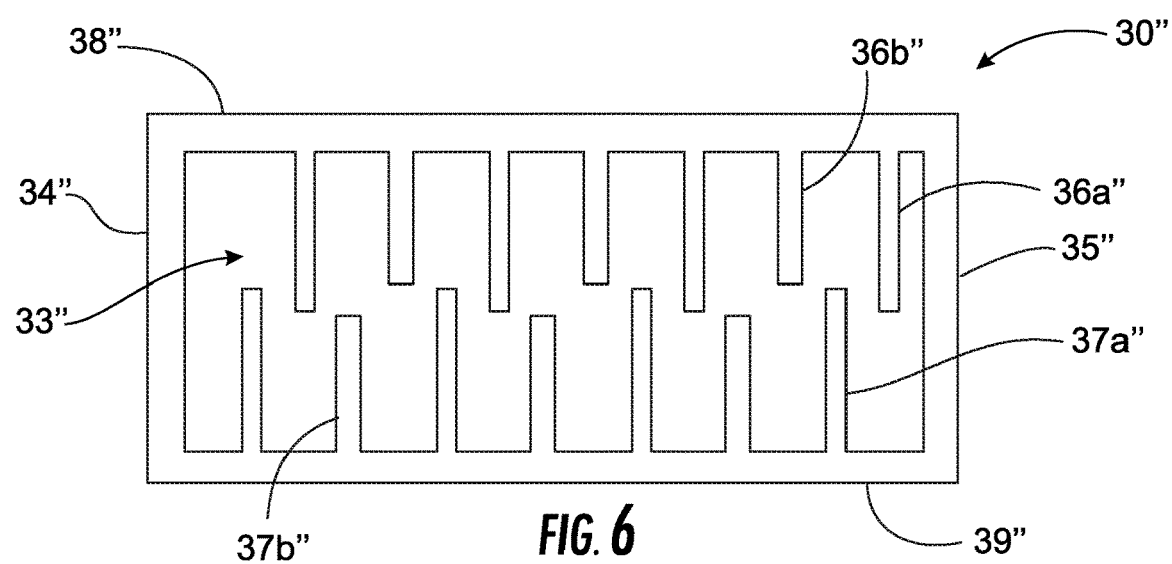
FIG. 6 is a cross-sectional view of yet another example embodiment of the bone cage of FIG. 2.

In accordance with another example embodiment of the bone cage 30" now described with reference to FIG. 6, different lengths of protrusions may also be used. More particularly, in the illustrated example the first protrusions alternate between long protrusions 36a" and short protrusions 36b". Similarly, the second protrusions alternate between long protrusions 37a" and short protrusions 37b". It should be noted that various different patterns of short and long protrusions may also be used, as well as intermediate lengths of protrusions in some embodiments, if desired.

Figure 7:
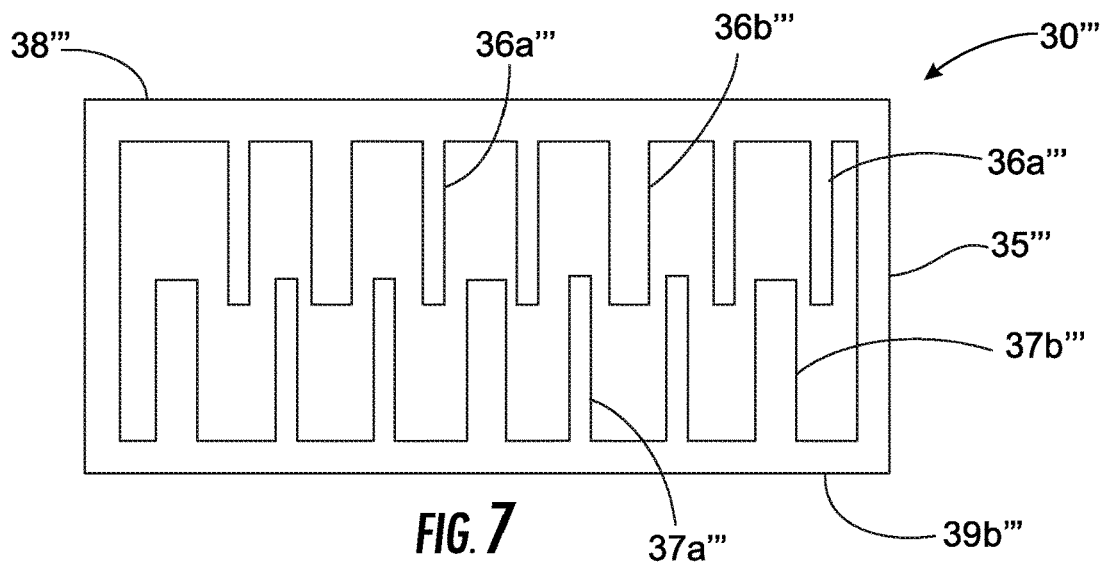
FIG. 7 is a cross-sectional view of another example embodiment of the bone cage of FIG. 2.

In still another example embodiment of the bone cage 30''' shown in FIG. 7, some of the protrusions have different widths. More particularly, in the illustrated example the first protrusions include both narrow protrusions 36a''' and wide protrusions 36b'''. Similarly, the second protrusions also include both narrow protrusions 37a''' and wide protrusions 37b'''. It should be noted that different patterns of protrusions having different widths may also be used in various embodiments, if desired.

The above-described bone cages advantageously allow for sufficient space within the bone ingrowth cavity to avoid restricting bone ingrowth, yet while also providing enough protrusions so that there is adequate surface area available for bone adhesion to provide sufficient rigidity and fusion. Moreover, since the first and second protrusions do not extend completely across the bone ingrowth cavity, in some embodiments the bone cages may be formed in separate pieces (e.g., upper and lower pieces) which are connected or fitted together before insertion. This may allow for greater ease of manufacturing in certain configurations, for example. Moreover, in some embodiments the above-described protrusions may have their own separate protrusions or branches to provide additional area for ingrowth or support.

A related method is also provided which may include installing one or more of the above-described bone cages 30, 30', 30", 30''', and/or 130 between adjacent bones in a patient. As noted above, this may be between adjacent vertebrae or other bones in a human or animal.

Many modifications and other embodiments will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included within the scope of the appended claims.

That which is claimed is:

1. A method for bone fusion for an immediately adjacent pair of vertebrae comprising:
    installing a bone cage between the immediately adjacent pair of vertebrae, the bone cage comprising
        first and second spaced apart frames each having a periphery and defining a bone ingrowth cavity therebetween inside the peripheries for receiving bone ingrowth from both of the immediately adjacent pair of vertebrae,
        a plurality of first rods each having a proximal end coupled to the first frame and a distal end extending into the bone ingrowth cavity toward the second frame but not contacting the second frame, and
        a plurality of second rods each having a proximal end coupled to the second frame and a distal end extending into the bone ingrowth cavity toward the first frame but not contacting the first frame,
        wherein the distal ends of the first rods are laterally offset from the distal ends of the second rods, and wherein the first rods do not contact the second rods within the bone ingrowth cavity.

2. The method of claim 1 wherein at least some of the first and second rods extend into the cavity at different angles.

3. The method of claim 1 wherein at least some of the first and second rods extend into the cavity normal to the first and second frames, respectively.

4. The method of claim 1 wherein at least some of the distal ends of the first and second rods extend past one another.

5. The method of claim 1 wherein at least some of the first and second rods have different widths.

6. The method of claim 1 wherein at least some of the first and second rods have different lengths.

7. The method of claim 1 wherein the first and second spaced apart frames comprise opposing upper and lower frames.

8. The method of claim 1 wherein the first and second spaced apart frames comprise opposing side frames.

9. The method of claim 1 wherein the first and second frames and the first and second rods comprise at least one of plastic, carbon fiber, and titanium.

10. A method for making a bone cage for bone fusion for an immediately adjacent pair of vertebrae comprising:
coupling first and second spaced apart frames together so that each has a periphery and defining a bone ingrowth cavity therebetween inside the peripheries for receiving bone ingrowth from both of the immediately adjacent pair of vertebrae;
the first frame having a plurality of first rods each having a proximal end coupled to the first frame and a distal end extending into the bone ingrowth cavity toward the second frame but not contacting the second frame; and
the second frame having a plurality of second rods each having a proximal end coupled to the second frame and a distal end extending into the bone ingrowth cavity toward the first frame but not contacting the first frame;
wherein the distal ends of the first rods are laterally offset from the distal ends of the second rods, and wherein the first rods do not contact the second rods within the bone ingrowth cavity.

11. The method of claim 10 wherein at least some of the first and second rods extend into the cavity at different angles.

12. The method of claim 10 wherein at least some of the first and second rods extend into the cavity normal to the first and second frames, respectively.

13. The method of claim 10 wherein at least some of the distal ends of the first and second rods extend past one another.

14. The method of claim 10 wherein at least some of the first and second rods have different widths.

15. The method of claim 10 wherein at least some of the first and second rods have different lengths.

16. The method of claim 10 wherein the first and second spaced apart frames comprise opposing upper and lower frames.

17. The method of claim 10 wherein the first and second spaced apart frames comprise opposing side frames.

18. The method of claim 10 wherein the first and second frames and the first and second rods comprise at least one of plastic, carbon fiber, and titanium.

* * * * *